US00PP13122P2

(12) United States Plant Patent
Heuger

(10) Patent No.: US PP13,122 P2
(45) Date of Patent: Oct. 22, 2002

(54) BEGONIA PLANT NAMED '00/2'

(76) Inventor: Joseph Heuger, Münsterstrasse 49, 49129 Glandorf (DE)

( * ) Notice: Subject to any disclaimer, the term of this patent is extended or adjusted under 35 U.S.C. 154(b) by 0 days.

(21) Appl. No.: 09/911,524

(22) Filed: Jul. 25, 2001

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Begonia plant named '00/2', characterized by its compact and upright plant habit; double pink-colored flowers with white to pale yellow centers that are held above the foliage; inner tepals with crenate margins; and excellent postproduction longevity.

1 Drawing Sheet

BACKGROUND OF THE INVENTION

The present Invention relates to a new and distinct cultivar of Begonia plant, botanically known as *Begonia×hiemalis,* commercially known as Elatior Begonia, and hereinafter referred to by the name '00/2'.

The new Begonia was discovered by the Inventor in a controlled environment in Glandorf, Germany, April, 2000, as a naturally-occurring whole plant mutation of *Begonia× hiemalis* 'Genie', disclosed in U.S. Plant patent application Ser. No. 09/778,206. The new Begonia was observed as a single plant in a group of flowering plants of the parent cultivar. The selection of this plant was based on its unique flower coloration.

Asexual reproduction of the new Begonia by cuttings taken in a controlled environment in Glandorf, Germany, has shown that the unique features of this new Begonia are stable and reproduced true to type in successive generations.

SUMMARY OF THE INVENTION

The cultivar '00/2' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of '00/2'. These characteristics in combination distinguish '00/2' as a new and distinct Begonia:

1. Compact and upright plant habit.
2. Double pink-colored flowers with white to pale yellow centers that are held above the foliage.
3. Inner tepals with crenate margins.
4. Excellent postproduction longevity.

Plants of the new cultivar are most similar to plants of the parent cultivar. In side-by-side comparisons conducted by the Inventor in Glandorf, Germany, plants of the new Begonia differ from plants of the cultivar Genie primarily in flower color as plants of the new Begonia have pink-colored flowers with white to pale yellow centers whereas plants of the cultivar Genie have soft salmon red and yellow bi-colored flowers.

Plants of the new cultivar differ primarily from plants of the cultivar 00/3, U.S. Plant Patent application filed concurrently with this application, in flower color as plants of the new cultivar have pink-colored flowers with white to pale yellow centers whereas plants of the cultivar 00/3 have orange red and yellow bi-colored flowers than fade to yellow.

BRIEF DESCRIPTION OF THE PHOTOGRAPHS

The accompanying colored photographs illustrate the overall appearance of the new Begonia, showing the colors as true as it is reasonably possible to obtain in colored reproductions of this type. Colors in the photographs may differ slightly from the color values cited in the detailed botanical description which accurately describe the colors of the new Begonia.

The photograph at the top of the sheet comprises a side perspective view of a typical flowering plant of '00/2'.

The photograph at the bottom of the sheet is a close-up view of typical flowers and leaves of '00/2'.

DETAILED BOTANICAL DESCRIPTION

In the following description, color references are made to The Royal Horticultural Society Colour Chart except where general terms of ordinary dictionary significance are used. The following observations and measurements describe plants grown in Glandorf, Germany, under commercial practice in a glass-covered greenhouse. Average day and night temperatures were 20° C. during the first three to four weeks then lowered to an average day and night temperature of 19° C. until flowering. Four weeks after planting in 13-cm containers, one week of long nyctoperiods of 16 hours were given followed by short nyctoperiods of eight hours until flowering. Plants used for the photographs and the description were about four months old. Measurements and numerical values represent averages for typical flowering plants.

Botanical classification: *Begonia×hiemalis* cultivar 00/2.
Commercial classification: Elatior Begonia.
Parentage: Naturally-occurring whole plant mutation of *Begonia×hiemalis* cultivar Genie, disclosed in U.S. Plant patent application Ser. No. 09/778,206.
Propagation:
*Type.*—Terminal cuttings.
*Time to develop roots.*—About 28 days at temperatures of 20° C.

*Root description.*—Fine, fibrous, well-branched and spreading. Plants of the new Begonia have not been observed to form tubers.

Plant description:

*Plant form.*—Compact; upright potted plant, inverted triangle; freely branching with good stem and stem base strength. Flowers are double and abundant. Plants flower continuously.

*Growth habit.*—Moderate growth rate, vigorous. Suitable for 11 to 15-cm containers. Under optimal environmental and cultural conditions, usually about 4 months are required to produce proportional 13-cm potted plants from terminal cuttings. About five vegetative shoots are formed at basal nodes and flowering shoots are formed at upper nodes.

*Plant height.*—About 24 cm.

*Plant width.*—About 32 cm.

*Leaves.*—Arrangement: Simple, alternate. Length: About 13.5 cm. Width: About 10 cm. Shape: Asymmetrical, more or less reniform. Apex: Acuminate. Base: Cordate. Margin: Doubly serrate. Texture: Glabrous. Venation pattern: Palmate. Color, young and fully expanded leaves: Upper surface: Darker than 147A. Lower surface: 194A, overlain with anthocyanin, 184A. Venation, upper and lower surfaces: 146C. Petiole length: About 5.5 cm. Petiole texture: Slightly pubescent. Petiole color: 181B.

Flower description:

*Flowering habit.*—Double flowers with numerous tepals arranged in axillary cymes. Usually 5 to 10 flowers per cyme. Many cymes in flower simultaneously. Flowers positioned above the foliage. Flowering continuous. Flowers self-cleaning, no fragrance.

*Natural flowering season.*—Plants will flower year around regardless of nyctoperiod, however plants flower earlier and more abundantly from mid-February until November in the Northern Hemisphere.

*Flowers.*—Shape: Rounded. Diameter: About 5.5 cm. Depth (height): About 2 cm.

*Flower buds.*—Length: About 1.75 cm. Diameter: About 2.5 cm. Color: 145D.

*Tepals.*—Arrangement: Rosette. Shape: Rounded flabellate, broad. Apex: Rounded. Margin: Two outer tepals, entire; inner tepals, crenate. Quantity per flower: Usually about 20 per flower. Size: Outer tepals: Length: About 3.5 cm. Width: About 4.4 cm. Inner tepals: Length: About 2.4 cm. Width: About 2.4 cm. Texture: Smooth, satiny, glabrous. Color: When opening: Towards apex of tepal, 53B; base, 155A; colors bleed together. Fully opened, upper surface: Towards apex of tepal, 52A; base, 11D; colors bleed together. Fully opened, lower surface: Towards apex of tepal, 54B; base, 155A; colors bleed together.

*Flower bracts.*—Arrangement: Two, opposite. Shape: Cordate, broad. Apex: Apiculate. Margin: Slightly serrate. Texture: Glabrous, smooth. Color, both surfaces: 144B.

*Peduncles.*—Angle: Erect. Length: About 5 cm. Texture: Glabrous. Color: 147C.

*Pedicels.*—Angle: Bent. Length: About 2.2 cm. Texture: Slightly pubescent. Color: Close to 144C.

*Reproductive organs.*—Stamens: None observed. Pistils: None observed.

*Seed.*—Seed production has not been observed as reproductive organs are not formed.

Postproduction longevity:

*Individual flowers.*—Generally about 2 to 3 weeks.

*Whole plants.*—About 6 weeks under interior conditions.

Disease/pest resistance: Resistance to pathogens and pests common to Begonia has not been observed.

It is claimed:

1. A new and distinct cultivar of Begonia plant named '00/2', as illustrated and described.

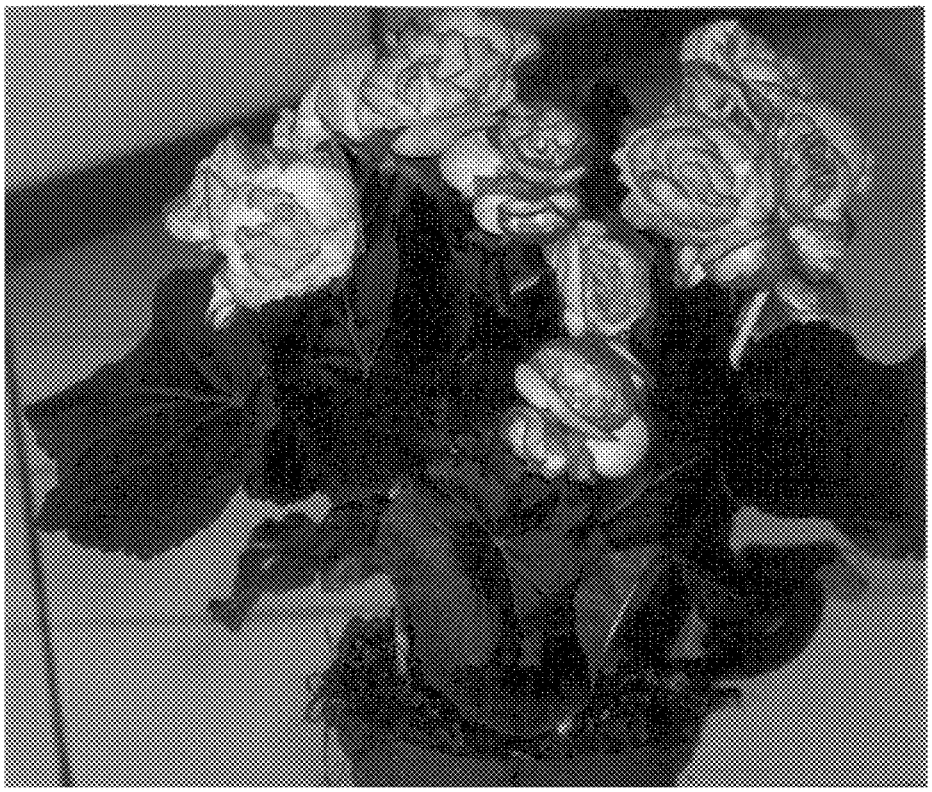
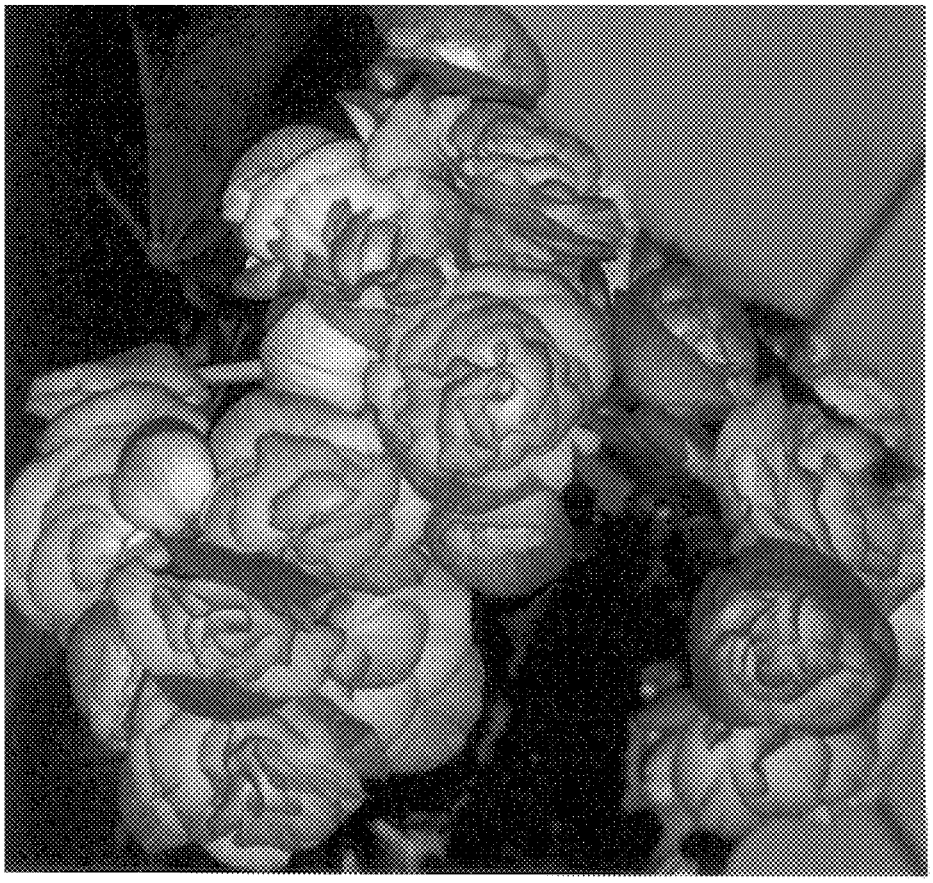

* * * * *